(12) United States Patent
Kendrick

(10) Patent No.: US 8,573,777 B1
(45) Date of Patent: Nov. 5, 2013

(54) EXAMINATION STAND WITH IMPROVED ACCESS FOR THE WHEELCHAIR BOUND PATIENT

(71) Applicant: Ophthalmology Associates of Northwestern Ohio, Inc., Maumee, OH (US)

(72) Inventor: Ronald M. Kendrick, Toledo, OH (US)

(73) Assignee: Opthamology Associates of Northwestern Ohio, Inc., Maumee, OH (US)

( * ) Notice: Subject to any disclaimer, the term of this patent is extended or adjusted under 35 U.S.C. 154(b) by 0 days.

(21) Appl. No.: 13/932,612

(22) Filed: Jul. 1, 2013

(51) Int. Cl.
*A61B 3/00* (2006.01)
*A61B 3/18* (2006.01)

(52) U.S. Cl.
CPC *A61B 3/0075* (2013.01); *A61B 3/18* (2013.01)
USPC .......................................... 351/245; 351/214

(58) Field of Classification Search
CPC ................................ A61B 3/0075; A61B 3/18
USPC .......................................... 351/200, 214, 245
See application file for complete search history.

(56) References Cited

U.S. PATENT DOCUMENTS

| 3,572,913 | A | * | 3/1971 | Korb et al. ..................... 351/245 |
| 5,580,023 | A | * | 12/1996 | Burton et al. ................. 248/430 |
| 5,609,316 | A | | 3/1997 | Tigliev |
| 7,670,003 | B2 | | 3/2010 | Kendrick |
| 2009/0027619 | A1 | * | 1/2009 | Kendrick ...................... 351/245 |

* cited by examiner

*Primary Examiner* — Huy K Mai
(74) *Attorney, Agent, or Firm* — Porter, Wright, Morris & Arthur, LLP

(57) ABSTRACT

A patient examination assembly comprises a rotatable stand adapted to mount a slit lamp microscope, and a phoropter attached to the stand by a telescoping arm assembly, comprising an arm and a connector, and the connector comprises a first link and a second link. The first link is telescopeable within the second link.

6 Claims, 2 Drawing Sheets

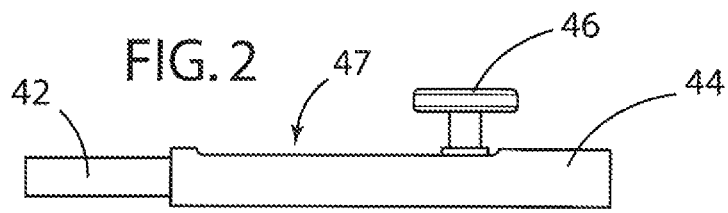
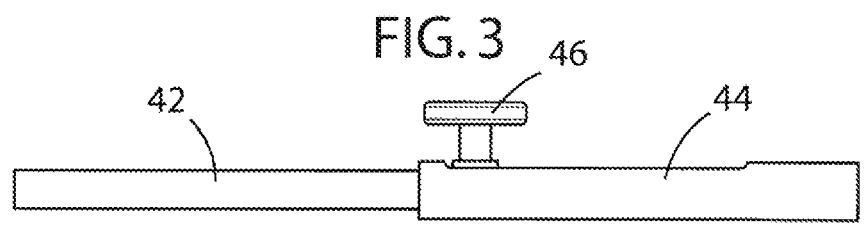
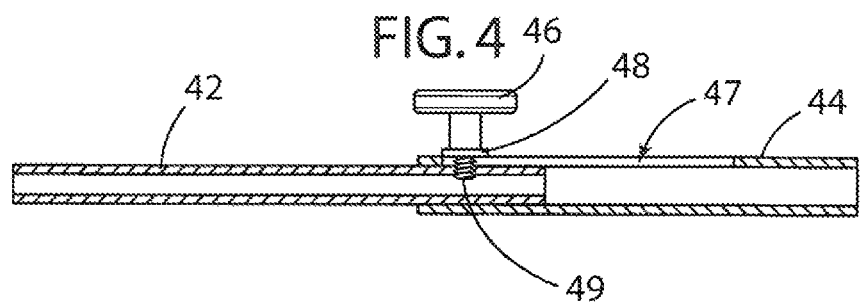
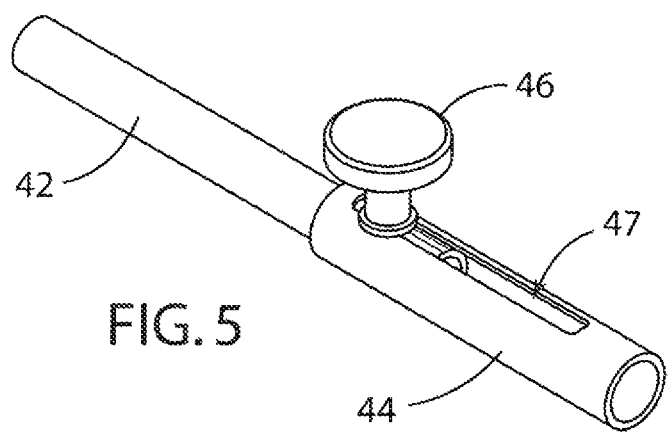

EXAMINATION STAND WITH IMPROVED ACCESS FOR THE WHEELCHAIR BOUND PATIENT

FIELD OF THE INVENTION

This invention relates to a stand for medical equipment and more particularly to a stand which improves access to the medical equipment for wheelchair bound patients.

BACKGROUND OF THE INVENTION

Medical equipment for examination of a patient sometimes comprises an examination chair, an instrument stand which supports some of the medical equipment, and a table connected to the stand via a series of adjustable arms. The table supports additional medical equipment, for example, a slit lamp biomicroscope. The slit lamp is an instrument consisting of a high-intensity light source that can be focused to shine as a slit. It is used in conjunction with a microscope. The lamp helps examination by allowing a doctor to look at the anterior segment, or frontal structures of the human eye, which includes the eyelid, sclera, conjunctiva, iris, natural crystalline lens, and cornea. The binocular slit-lamp examination provides stereoscopic magnified view of the eye structures in striking detail, enabling exact anatomical diagnoses to be made for many eye conditions. Combined with special lenses the examination of retinal structures can be accomplished in detail. While a patient is seated in the examination chair, he rests his chin and forehead on a support (chin strap) to steady the head. Using the biomicroscope, the optometrist or ophthalmologist then proceeds to examine the patients eye. The slit lamp is mounted on the table, which is in turn adjustably connected to the stand. This adjustability allows the doctor to treat patients of varying heights and sizes.

However, known medical equipment stands have several limitations in the range of patients which can be conveniently examined, especially with respect to patients confined to a wheelchair. For example, the table is typically too wide to be placed between the arms of a standard wheelchair. Also, legs connecting the stand to the table were previously designed to work with an examination chair which is much higher than standard wheelchairs, and therefore cannot get low enough to examine a patient bound to a wheelchair. Moreover, the legs have previously been attached to the table on the underside of the table near the center of the table, such that the legs partially obstructs area below the table, requiring the table to be raised to clear over a patient's lower body, for example. Typically all of this would require a wheelchair bound patient to be lifted out of his wheelchair and moved to a separate examination chair. Clearly, this makes known medical equipment stands inconvenient for wheelchair bound patients. While some examination stands have examination chairs which are movable along a track, this is not a practical option when the examination room is relatively small, as is often the case with ambulatory surgical facilities.

U.S. Pat. No. 7,670,003 to Kendrick, assigned to the assignee of the present invention addresses several of these problems with an elegant leg assembly which can reach to the wheelchair bound patient and which also reduces the size of the table such that it fits between the arms of the wheelchair. However, the phoropter (the instrument used by optometrists and ophthalmologists to measure an individuals refractive error and to determine his eyeglass prescription) of many off the shelf ophthalmic examination stands may, in some instances, still be unable to be conveniently accessed by a wheelchair bound patient. It would be desirable to provide a patient examination assembly where all medical equipment is convenient for essentially all patients, including wheelchair bound patients.

SUMMARY OF THE INVENTION

In accordance with a first aspect, a patient examination assembly comprises a rotatable stand adapted to mount a slit lamp microscope, and a phoropter attached to the stand by a telescoping arm assembly, comprising an arm and a connector, and the connector comprises a first link and a second link. The first link is telescopeable within the second link.

From the foregoing disclosure and the following more detailed description of various preferred embodiments it will be apparent to those skilled in the art that the present invention provides a significant advance in the technology and art of stands for medical equipment. Particularly significant in this regard is the potential the invention affords for providing a high quality, low cost, easy to use stand adapted for specialized design constraints, including wheelchair bound patients. Additional features and advantages of various preferred embodiments will be better understood in view of the detailed description provided below.

BRIEF DESCRIPTION OF THE DRAWINGS

FIG. 2 is an isolated schematic side view of a telescoping arm assembly shown in a retracted position.

FIG. 3 is an isolated schematic side view of the telescoping arm assembly of FIG. 2, shown in an extended position.

FIG. 4 is a cross section view of the telescoping arm assembly of FIG. 3.

FIG. 5 is an isometric view of the telescoping arm assembly of FIG. 2.

Figure 1:
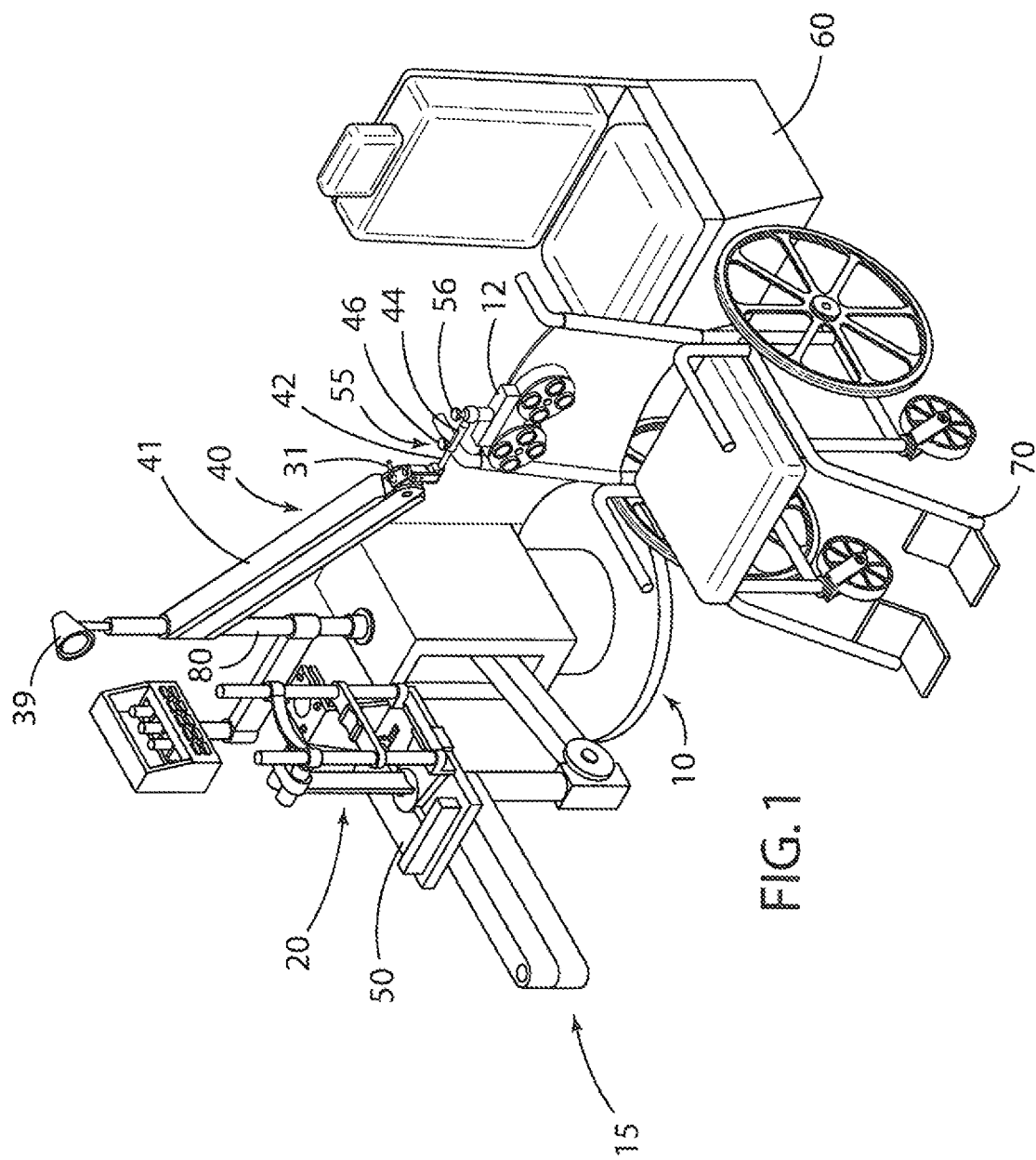
FIG. 1 is a schematic perspective view of one embodiment of a patient examination assembly, where a phoropter is adjustably mounted on the end of an arm assembly.

It should be understood that the appended drawings are not necessarily to scale, presenting a somewhat simplified representation of various preferred features illustrative of the basic principles of the invention. The specific design features of the patient examination assembly as disclosed here will be determined in part by the particular intended application and use environment. Certain features of the illustrated embodiments have been enlarged or distorted relative to others to help visualization and clear understanding. In particular, thin features may be thickened, for example, for clarity of illustration. All references to direction and position, unless otherwise indicated, refer to the orientation illustrated in the drawings.

DETAILED DESCRIPTION OF CERTAIN EMBODIMENTS

It will be apparent to those skilled in the art, that is, to those who have knowledge or experience in this area of technology, that many uses and design variations are possible for the medical equipment/examination stand disclosed here. The following detailed discussion of various alternative and preferred features and embodiments will illustrate the general principles of the invention with reference to a stand for use with an ophthalmic slit lamp and related ophthalmic equipment. Other embodiments suitable for other applications, such as a stand for use with an ocular blood flow analyzer will be apparent to those skilled in the art given the benefit of this disclosure.

Referring now to the drawings, FIG. 1 shows a patient examination assembly in accordance with a preferred embodiment. A stand 10, preferably rotatable about a vertical axis, supports medical equipment. In FIG. 1, some of the medical equipment can comprise, for example, a slit lamp biomicroscope 20, mounted on a table 50, the phoropter 12 (the instrument used by optometrists and ophthalmologists to measure an individual's refractive error and determine his eyeglass prescription) operatively connected to the stand via post 80, with light 39 to illuminate an eye chart, and a control panel and storage chamber. The slit lamp biomicroscope 20 may be extendable via leg assembly 15 to a patient in a wheelchair 70 positioned in front of the standard chair that is part of the patient examination assembly, and the table 50 may be sufficiently narrow to fit between the arms of the wheelchair. In this way the wheelchair bound patient need not be forced to leave his wheelchair to get into the standard chair in order to be examined by the physician with the equipment of the examination assembly.

Existing patient examination assemblies have a phoropter mounted on an arm which can be adjusted about the post and about a vertical axis (with knob 56) with respect to the ground to the accommodate patient seated in the standard chair. Since wheelchairs come in standard sizes, standard arm assemblies are designed to accommodate the distance from the post 80 to the phoropter. However, when a wheelchair bound patient is positioned in a wheelchair, the distance from the post to the phoropter needs to be increased by about 18-26 inches, more preferably about 22 inches to extend to a position where a wheelchair bound patient would normally not have to contort or twist to position his body correctly. In this situation, the existing arm is too short to reach comfortably. In accordance with a highly advantageous feature, a telescopable arm assembly 40 operatively connects the post, allowing the phoropter to extend to the wheelchair. The arm assembly can comprise, for example, an arm 41 and a connector 55. Since many patient examination stands are already in use, it would be desirable to provide a stand based on the existing stands and retrofitted to make the phoropter accessible to wheelchair bound patients. In existing stands, the arm is pivotably attached to the post. Therefore, in the embodiment of FIG. 1, the arm 41 is also pivotably attached to the post 80, and the connector 55 is telescopable and attached to the phoropter 12, although it will be readily understood to those skilled in the art, given the benefit of this disclosure, that this arrangement can be reversed with the telescoping elements positioned between the post and the arm.

As shown in greater detail in FIGS. 2-5, the connector 55 comprises a first link 42 and a second link 44. Each of these links can have a generally cylindrical tube portion with one tube sliding into another to move between a retracted position (shown in FIG. 2) and an extended position (shown in FIG. 3). In this embodiment the first link 42 has a smaller diameter than the second link 44, and is telescopable inside the second link. A slot 47 may be defined by the second link 44. A knob 46 is operatively connected with an engagement element such as a screw 49. The knob is rotatable from a tightened position where the screw 49 extends into an opening of the first link 42 as shown in FIG. 4, to a loosened position where the screw is not in the opening of the first link. In the loosened position the first link is translatable with respect to the second link, and more specifically telescopable within the second link. Then, when the first link is in a desired position, the knob can be rotated to have the screw reenter the opening of the first link to hold the links together in a tightened position so that they do not move with respect to one another. Optionally a washer 48 may be positioned between the knob 46 and the links.

From the foregoing disclosure and detailed description of certain embodiments, it will be apparent that various modifications, additions and other alternative embodiments are possible without departing from the true scope of the invention. The embodiments discussed were chosen and described to provide the best illustration of the principles of the invention and its practical application to thereby enable one of ordinary skill in the art to use the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A patient examination assembly comprising, in combination:
   a rotatable stand adapted to mount a slit lamp microscope; and
   a phoropter attached to the stand by a telescoping arm assembly, comprising an arm and a connector, and the connector comprises a first link and a second link wherein the first link is telescopeable within the second link.

2. The patient examination assembly of claim 1 wherein the arm is pivotably connected to the stand, and the first link is attached to the arm and the second link is attached to the phoropter.

3. The patient examination assembly of claim 2 further comprising a knob operatively connected to the second link, wherein the knob is rotatable from a tightened position which restricts relative motion of the second link with respect to the first link, to a loosened position where the second link can translate with respect to the first link.

4. The patient examination assembly of claim 3 further comprising a post extending from the stand, wherein the arm is attached to the post.

5. The patient examination assembly of claim 4 wherein the first link is telescopable inside the second link.

6. The patient examination assembly of claim 5 wherein the first link defines an opening, the second link defines a slot and the knob is operatively connected to an element which extends through the slot and into the opening to releasably secure the first link to the second link.

* * * * *